(12) United States Patent
Douglass et al.

(10) Patent No.: US 8,372,064 B2
(45) Date of Patent: Feb. 12, 2013

(54) ARTICULATABLE DEVICE FOR DELIVERING THERAPEUTIC ENERGY TO TISSUE

(75) Inventors: Valerie L. Douglass, Mountain View, CA (US); Robert M. Pearson, San Jose, CA (US); James G. Lovewell, San Leandro, CA (US); David A. Blau, Cupertino, CA (US)

(73) Assignee: AngioDynamics, Inc., Latham, NY (US)

( * ) Notice: Subject to any disclaimer, the term of this patent is extended or adjusted under 35 U.S.C. 154(b) by 788 days.

(21) Appl. No.: 12/267,307

(22) Filed: Nov. 7, 2008

(65) Prior Publication Data

US 2009/0125019 A1    May 14, 2009

Related U.S. Application Data

(60) Provisional application No. 60/986,472, filed on Nov. 8, 2007.

(51) Int. Cl.
*A61B 18/18* (2006.01)
(52) U.S. Cl. .......................... 606/19; 606/41
(58) Field of Classification Search .............. 606/41, 606/256, 19; 607/96, 113
See application file for complete search history.

(56) References Cited

U.S. PATENT DOCUMENTS

| | | | |
|---|---|---|---|
| 5,368,564 A * | 11/1994 | Savage | 604/95.04 |
| 5,441,499 A * | 8/1995 | Fritzsch | 606/45 |
| 5,916,213 A * | 6/1999 | Haissaguerre et al. | 606/41 |
| 7,387,628 B1 * | 6/2008 | Behl et al. | 606/41 |
| 2004/0059328 A1 * | 3/2004 | Daniel et al. | 606/41 |
| 2004/0267326 A1 * | 12/2004 | Ocel et al. | 607/9 |
| 2005/0090809 A1 * | 4/2005 | Cooper et al. | 606/1 |
| 2006/0094931 A1 * | 5/2006 | Danitz et al. | 600/141 |
| 2007/0043397 A1 * | 2/2007 | Ocel et al. | 607/10 |
| 2007/0055327 A1 | 3/2007 | Esch | |
| 2007/0078455 A1 * | 4/2007 | Rashidi | 606/41 |
| 2007/0179575 A1 | 8/2007 | Esch | |
| 2007/0191829 A1 * | 8/2007 | McGee et al. | 606/41 |
| 2008/0140070 A1 * | 6/2008 | Filloux et al. | 606/41 |
| 2008/0167649 A1 * | 7/2008 | Edwards et al. | 606/41 |

OTHER PUBLICATIONS

PCT International Search Report of the International Searching Authority for PCT/US2008/082893 dated May 21, 2009.

* cited by examiner

*Primary Examiner* — Nicholas Lucchesi
*Assistant Examiner* — Gerald Landry, II
(74) *Attorney, Agent, or Firm* — Tara L. Clothier

(57) ABSTRACT

A device for delivering therapeutic energy to tissue is provided. The device includes a proximal segment and a distal segment having one or more electrodes for delivering the therapeutic energy to the tissue. An articulating segment connects the proximal segment and the distal segment such that the distal segment is articulatable with respect to a longitudinal axis of the proximal segment. In one aspect of the invention, the articulating segment includes a living hinge. In another aspect of the invention, at least one electrically conductive articulating cable runs along the articulating segment, wherein the articulating cable is used both to articulate the distal segment and to deliver the therapeutic energy to the one or more electrodes.

19 Claims, 10 Drawing Sheets

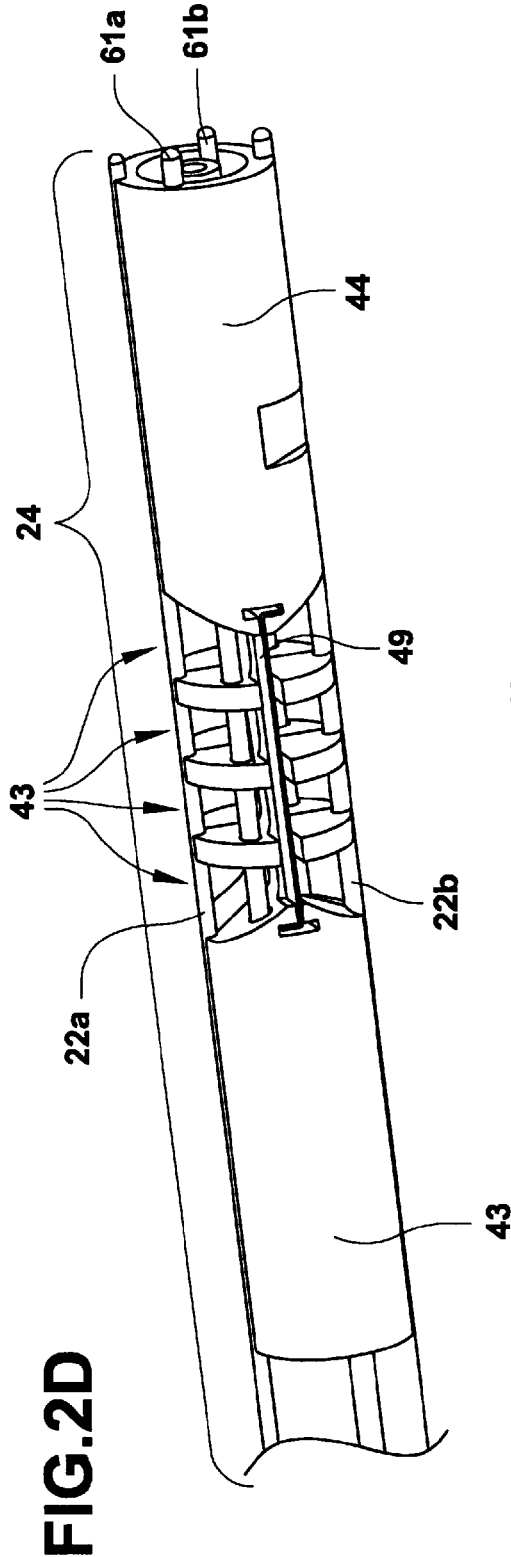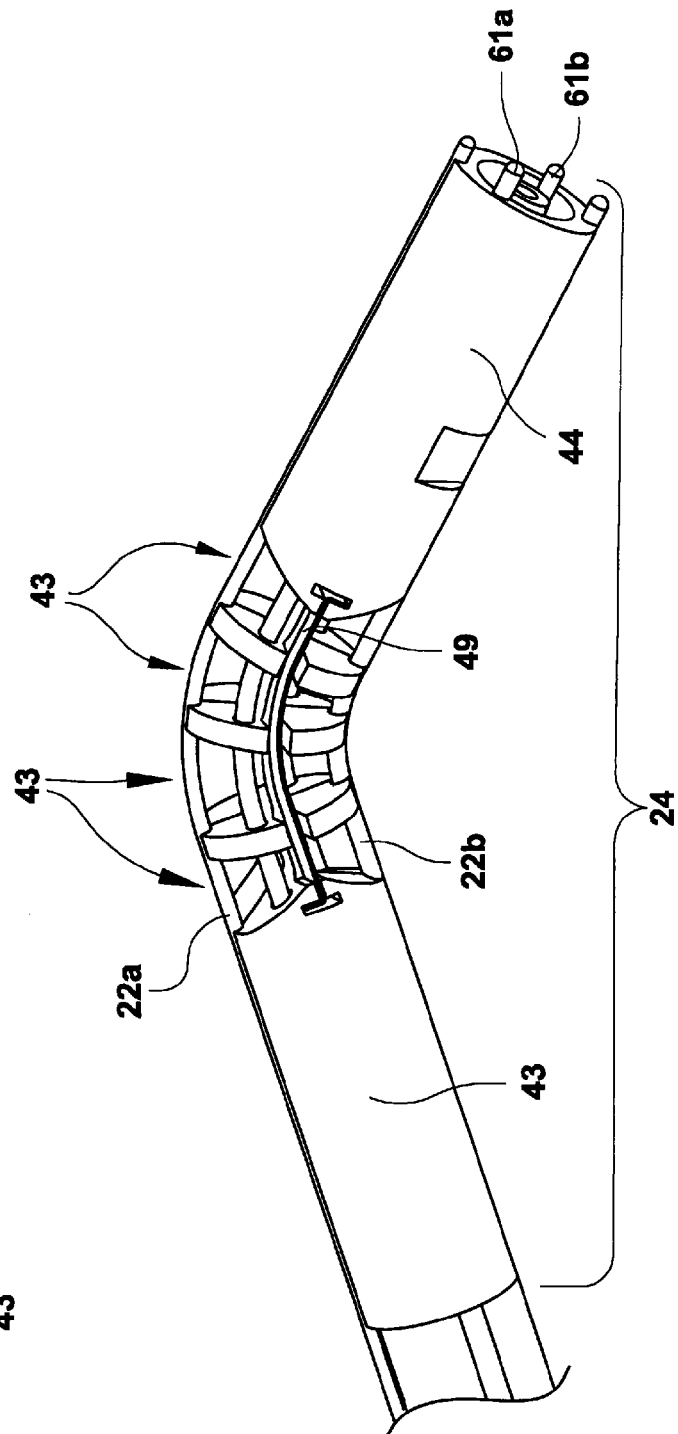
FIG.2D
FIG.2E

ARTICULATABLE DEVICE FOR DELIVERING THERAPEUTIC ENERGY TO TISSUE

CROSS REFERENCE TO RELATED APPLICATIONS

This application claims the benefit of priority under 35 U.S.C. Section 119(e) to U.S. Provisional Application Ser. No. 60/986,472, filed Nov. 8, 2007, entitled "Medical Devices And Methods Of Using The Same", which is fully incorporated by reference herein.

This application is also related to co-pending U.S. application Ser. No. 12/267,403 filed on Nov. 7, 2008, which is incorporated herein by reference.

FIELD OF THE INVENTION

The present invention relates to a medical device and method for the ablation of diseased tissue. More particularly, the present application relates to a device for delivering therapeutic energy to tissue, and methods for using the same.

BACKGROUND OF THE INVENTION

Conventional devices for delivering therapeutic energy to tissue include a handle and a probe coupled to the handle. The probe contains at least one electrode to which an electrical power source is connected. The power source allows the electrode to deliver the therapeutic energy to a targeted tissue, thereby causing ablation of the tissue.

With currently available devices for delivering therapeutic energy to tissue, they are hard to maneuver inside a body. It is often difficult or sometimes not possible to place the probe in the correct location of the tissue to be ablated. This is especially a problem when the probe is used inside a laparoscopic device.

Therefore, it would be desirable to provide a device and method which is more maneuverable inside a body.

SUMMARY OF THE DISCLOSURE

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

Disclosed herein are devices for delivering therapeutic energy for destruction and/or removal of undesirable living biological tissues and methods of using such, particularly for treatment. In particular, according to the principles of the present invention, a device for delivering therapeutic energy to tissue is provided. The device includes a proximal segment and a distal segment having one or more electrodes for delivering the therapeutic energy to the tissue. An articulating segment connects the proximal segment and the distal segment such that the distal segment is articulatable with respect to a longitudinal axis of the proximal segment. In one aspect of the invention, the articulating segment includes a living hinge. In another aspect of the invention, at least one electrically conductive articulating cable runs along the articulating segment, wherein the articulating cable is used both to articulate the distal segment and to deliver the therapeutic energy to the one or more electrodes.

BRIEF DESCRIPTION OF THE DRAWINGS

FIG. 2D is a plan view of an additional embodiment of an articulating segment of the therapeutic energy delivery device of the present invention.

FIG. 2E is a plan view of the articulating segment of FIG. 2D being shown in an articulated position.

DETAILED DESCRIPTION OF THE INVENTION

Figure 1A:
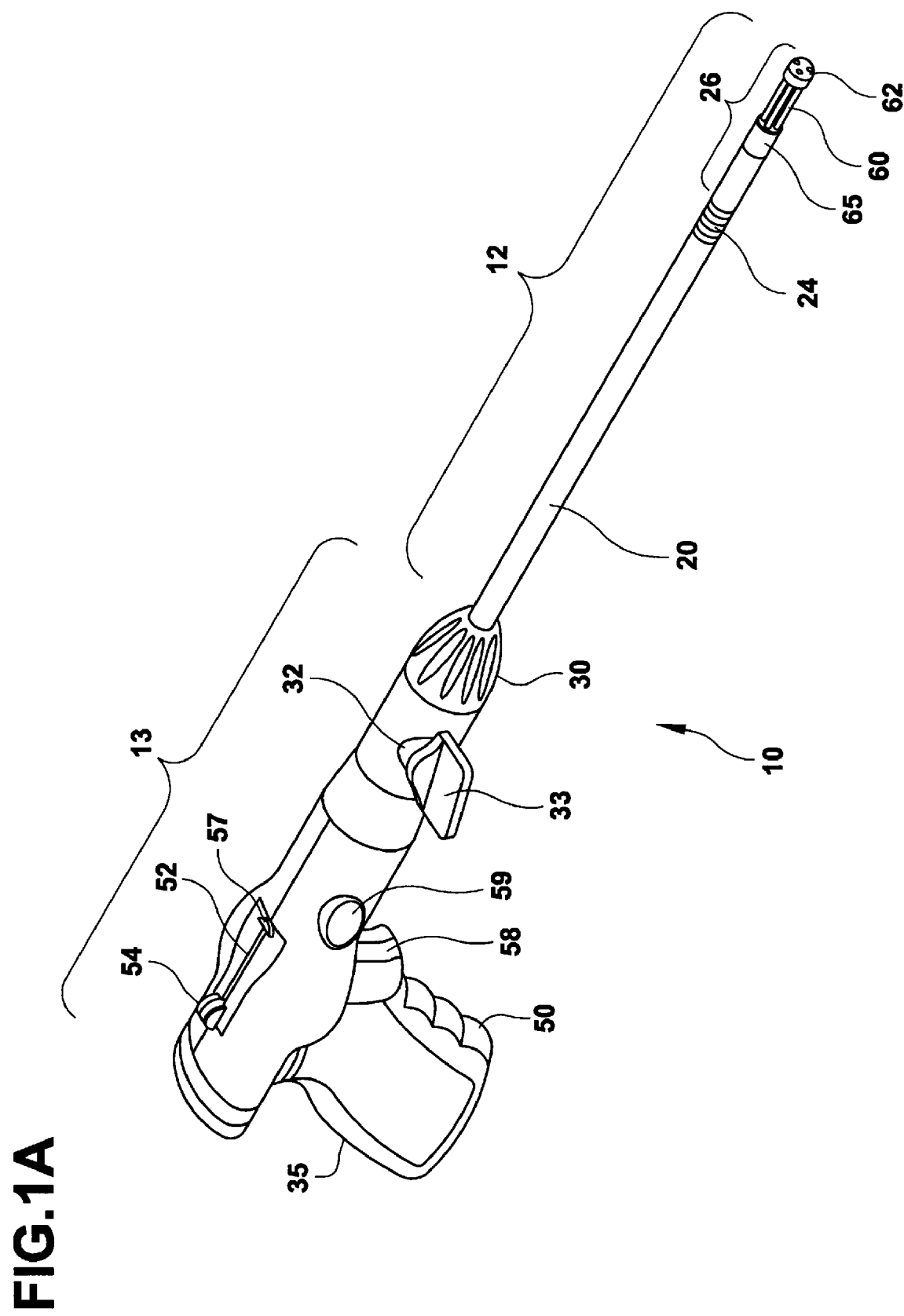
FIG. 1A is a perspective view of a therapeutic energy delivery device of the present invention.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Thus, for example, the reference to a microparticle is a reference to one such microparticle or a plurality of such microparticles, including equivalents thereof known to one skilled in the art. Also, as used herein and in the claims, the terms "at least one" and "one or more" have the same meaning and include one, two, three or more. The following terms, unless otherwise indicated, shall be understood to have the following meanings when used in the context of the present disclosure.

"Therapeutic energy" and "TE", used interchangeably herein and in the contexts of "therapeutic energy delivery" and "TED" as well as "therapeutic energy conversion" and "TEC", refer to the energy output from the treatment member(s) of the devices or portions thereof (e.g., distal segment(s) of the treatment member(s)) to its immediate surroundings, such as the target tissue(s) when present. Energy output from a power source, prior to its modification by the devices, is not considered to be therapeutic energy. Non-limiting examples of therapeutic energy include electromagnetic energy such as radio frequency energy, radiant thermal energy, radiation energy, acoustic energy (e.g., ultrasonic energy), and combinations of two or more thereof.

"Radio frequency" and "RF", used interchangeably, refer to electromagnetic waves having a frequency of 3 GHz or less, such as between 500 MHz and 3 GHz (microwaves), 100 MHz or less, 10 MHz or less, 1 MHz or less, optionally 10 kHz or greater, such as 100 kHz or greater.

"Operator" refers to a person or a robotic assembly who uses the devices for treatments, particularly in patients (e.g., coagulation, ablation). The operator may be a physician, including interventional radiologists, oncologists, and surgeons.

"Polymer" or "polymeric" refers to a natural, recombinant, synthetic, or semisynthetic molecule having in at least one main chain, branch, or ring structure two or more repeating monomer units. Polymers broadly include dimers, trimers, tetramers, oligomers, higher molecular weight polymers, adducts, homopolymers, random copolymers, pseudocopolymers, statistical copolymers, alternating copolymers, periodic copolymers, bipolymers, terpolymers, quaterpolymers, other forms of copolymers, substituted derivatives thereof, and mixtures thereof, and narrowly refer to molecules having or more repeating monomer units. Polymers can be linear, branched, block, graft, monodisperse, polydisperse, regular, irregular, tactic, isotactic, syndiotactic, stereoregular, atactic, stereoblock, single-strand, double-strand, star, comb, dendritic, and/or ionomeric, can be ionic or non-ionic, can be neutral, positively charged, negatively charged, or zwitterionic, and can be used singly or in combination of two or more thereof.

Other than in the operating examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values can be used.

"Formed from" and "formed of" denote open claim language. As such, it is intended that a member "formed from" or "formed of" a list of recited components and/or materials be a member comprising at least these recited components and/or materials, and can further include other non-recited components and/or materials.

Examples provided herein, including those following "such as" and "e.g.," are considered as illustrative only of various aspects and features of the present disclosure and embodiments thereof, without limiting the scope of any of the referenced terms or phrases either within the context or outside the context of such descriptions. Any suitable equivalents, alternatives, and modifications thereof (including materials, substances, constructions, compositions, formulations, means, methods, conditions, etc.) known and/or available to one skilled in the art can be used or carried out in place of or in combination with those disclosed herein, and are considered to fall within the scope of the present disclosure. Throughout the present disclosure in its entirety, any and all of the one, two, or more features and aspects disclosed herein, explicitly or implicitly, following terms "example", "examples", "such as", "e.g.", and the likes thereof may be practiced in any combinations of two, three, or more thereof (including their equivalents, alternatives, and modifications), whenever and wherever appropriate as understood by one of ordinary skill in the art. Some of these examples are themselves sufficient for practice singly (including their equivalents, alternatives, and modifications) without being combined with any other features, as understood by one of ordinary skill in the art. Therefore, specific details disclosed herein are not to be interpreted as limiting, but merely as a basis for the claims and as a representative basis for teaching one skilled in the art to variously employ aspects and features of the present disclosure in virtually any appropriate manner.

The present invention is illustrated in FIGS. 1 through 6D. A therapeutic energy delivery device 10 is illustrated in FIG. 1A. A treatment member 12 delivers the therapeutic energy to tissue. Treatment member 12 may adopt an elongated configuration, as illustrated herein, such as in the general shape of a trocar, a probe, a needle, a cannula, an antenna, or the likes thereof that is commonly used in the medical profession. Treatment member 12 has a distal end that may or may not be able to penetrate soft tissues, or be able to adopt either configuration as disclosed herein.

Treatment member 12 includes a proximal segment 20 and a distal segment 26. Treatment member 12 of the TED devices may have a diameter of 1 mm or greater and/or 100 mm or less, such as 5 mm, 8 mm, 10 mm, 15 mm, 20 mm, or in a range between any two of such values. Treatment member 12 may have a longitudinal length of 5 cm or greater and/or 100 cm or less, such as 10 cm, 20 cm, 30 cm, 35 cm, 40 cm, 45 cm, 50 cm, 60 cm, 70 cm, 80 cm, 90 cm, or in a range between any two of such values. Distal segment 26 of the TED devices may have a longitudinal length of 0.5 cm or greater and/or 50 cm or less, such as 1 cm, 5 cm, 6 cm, 7 cm, 8 cm, 9 cm, 10 cm, 11 cm, 12 cm, 15 cm, 20 cm, 30 cm, or in a range between any two of such values.

The distal segment 26 includes one or more electrodes 60 (e.g., two, three, four, or more electrodes, optionally aligned in parallel with each other) for delivering the therapeutic energy to the tissue. Certain TED devices disclosed herein may have two TED elements (such as electrodes) or less, suitable for relatively small resection lines. Certain TED devices disclosed herein may have four TED elements (such as electrodes) or more, suitable for resections where speed is more of a concern than size. TED elements 60 of the TED devices may have an exposable longitudinal length of 0.5 cm or greater and/or 10 cm or less, such as 1 cm, 2 cm, 2.5 cm, 3 cm, 4 cm, 5 cm, 6 cm, 8 cm, or a range between any two of such values.

The distal segment 26 may further include a guard piece 62. Guard piece 62 may be round-ended (e.g., substantially hemi-spheroidal or bullet-shaped), and may be present for shielding healthy tissues from tissue-piercing ends of certain embodiments of electrodes 60. Guard piece 62 may be retractable as described herein, allowing pointed electrodes 60 to be exposed for insertion into the target tissue. Guard piece 62, when it is locked to shield pointed tips of TED elements 60, may withstand a compression force of at least 1 lb before failure (exposure of pointed tip) occurs so as to prevent unintended tissue-piercing during introduction of treatment member 12.

As will be discussed in further detail below, the distal segment 26 may further include a therapeutic energy conversion (TEC) portion 65.

Proximal segment 20 and distal segment 26 may be substantially similar in rigidity. An articulating segment 24 is connected between the proximal segment 20 and the distal segment 26 such that the distal segment 26 is articulatable with respect to a longitudinal axis of the proximal segment 20. Distal segment 26 may be able to cover at least one circular sector having a central angle of $\pi/6$ radians or 15 greater, the at least one circular sector being symmetric with respect to the longitudinal axis of main segment 20. The central angle of the at least one circular sector coverable by articulatable TED segment 26 may be $\pi/3$ radians or greater, or $\pi/2$ radians or greater, or $2\pi/3$ radians or greater, or $5\pi/6$ radians or greater, or $\pi$ radians or greater, or in a range between any two of such values.

Proximal to treatment member 12, device 10 may include a base 13 for an operator to manipulate treatment member 12 or portions thereof (e.g., the distal segment 26 and the guard piece 62, among others). The base 13 may include a handle 35 that includes a gripping section 50 and a trigger 58. A collar 30 is rotatably coupled to the base, wherein rotation of the collar 30 rotates the proximal segment 20 about its longitudinal axis. Collar 30, when reticulated, may be locked in one or more pre-set angles or in any angle desired or adjusted by the operator. The base 13 may have a side port 32 for coupling to a turning knob 33. Other visible features on handle 35 may include a portion of a trigger slide 57, a lever portion of a retraction lock 54 (slidable, when depressed, along a slot 52), and a therapeutic energy delivery switch actuator 59 (which includes push buttons on both sides of base 13) that turns device 10 on or off.

It is noted that a continuous tubular sheath, made of biologically compatible materials (e.g., stainless steel, titanium, alloys thereof), may surround the proximal segment 20, articulation segment 24, and distal segment 26, as shown in FIG. 1A. The tubular sheath operates to protect the components of treatment member 12 when they are positioned within a patient during a procedure. Features such as a spiral cut may be fashioned along the tubular sheath over the articulating segment 24 to provide the required flexibility thereto.

TED devices may be constructed to be robust, for example, having one or more of the following characteristics: a tensile strength of 1-5 lb or more from TED 10 elements 60 to handle 35; a torque of 0.1-0.5 in-lbs or more between TED elements 60 and handle 35; a bending moment of 1-4 in-lbs or more between TED elements 60 and main segment 20; a resistance of 1-4 in-lbs or more for articulation segment 24 in a nonarticulating direction; a bending moment of 5-20 in-lbs or more between proximal segment 20 and base 13.

Distal segment 26, when articulated, may be locked in one or more pre-set angles or in any angle desired or adjusted by the operator. Such a locking mechanism may withstand a compression and/or torque force of 1-2 lbs or more exerted at handle 35 before failure occurs. When distal segment 26 is at maximal articulation angle (e.g., 75 degrees or greater), articulation segment 24 may withstand a compression and/or torque force of 1-2 lbs or more exerted at handle 35 before failure occurs. Alternatively or in addition, articulation segment 24 may allow the distal end of distal segment 26 to arc 0.5 inches or less before breaking free of the locked angle.

TED devices and components therein may be able to withstand exposure to 2× ethylene oxide sterilization without incurring functional failures. TED devices and components therein may be substantially biocompatible.

TED devices disclosed herein may be used in monopolar configurations and/or bipolar configurations. The geometry of resulting ablation/resection volumes may depend at least in part on the configuration of TED elements 60. For example, with a linear arrangement of two or more electrodes, the ablation volume may have a minimum diameter of 1 mm to 2 mm, such as 1.8 mm. With a two-dimension arrangement of four or more electrodes, the ablation volume may have a major cross-section, at a minimum, of 5×5 mm to 10×10 mm, such as 8×8 mm. TED devices may be activated by switch 70 (FIG. 3) through depression of switch actuator 59 on base 13. Alternatively or in combination, TED devices may be activated by one or more foot pedals.

Figure 1B:
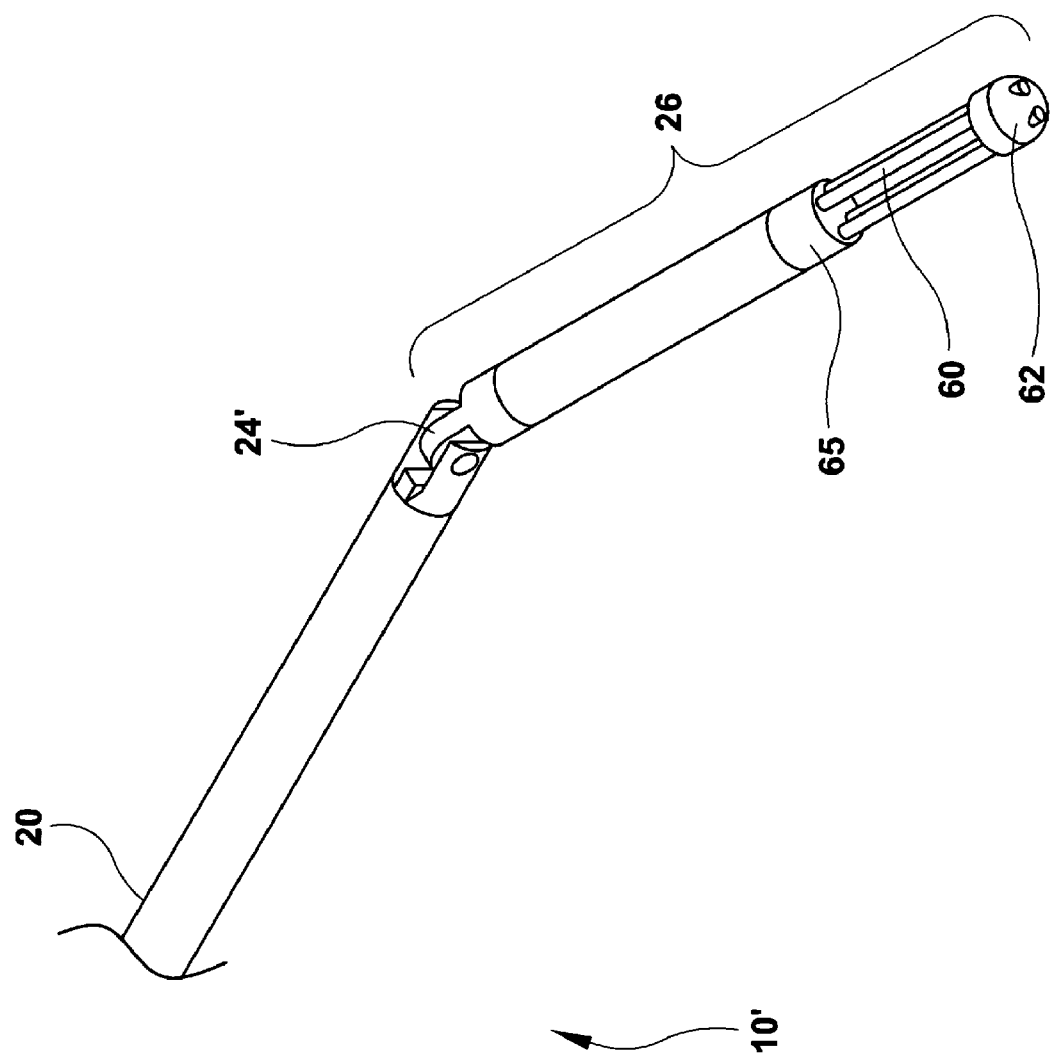
FIG. 1B is a perspective view of an additional embodiment of the distal end of the therapeutic energy delivery device of the present invention.

FIG. 1B illustrates the distal end of an additional embodiment of the therapeutic energy delivery device 10' of the present invention. In this embodiment, the articulating segment 24' includes a common hinge joint. In this way, the distal segment 26 is articulatable with respect to a longitudinal axis of the proximal segment 20.

Figure 2A:
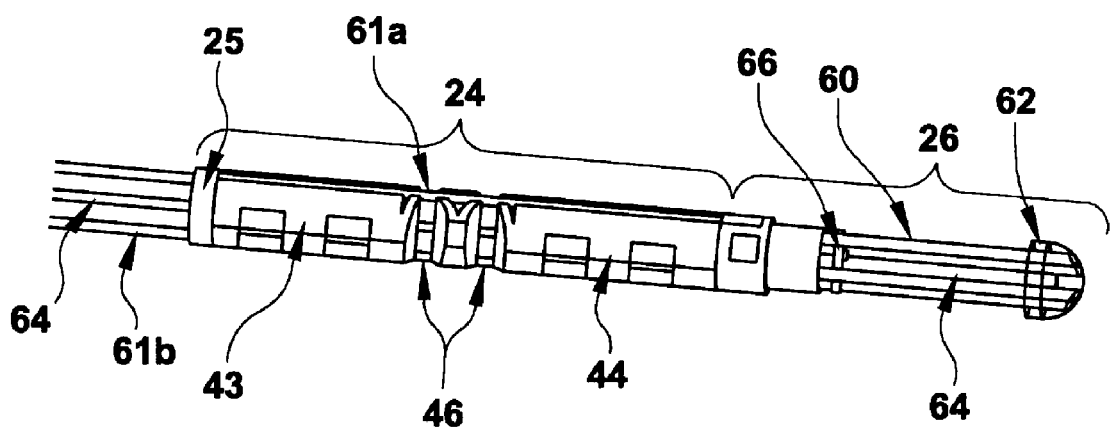
FIG. 2A is a plan view of an additional embodiment of the distal end of the therapeutic energy delivery device of the present invention.

FIG. 2A illustrates an additional embodiment of the articulating segment 24 of FIG. 1A, wherein the articulating segment 24 is a living hinge. The living hinge 24 may have a proximal portion 43 that is connected to the proximal segment 20 (FIG. 1A); and a distal portion 44 that is connected to the distal segment 26. Near the middle section of the living hinge 24, there are two longitudinally spaced recessed portions 46 that define where the articulation occurs. It should be noted that the living hinge may include any number of recessed portions, including one, two, three, four or more. One or more articulating cables 22a, 22b (see FIGS. 2C-2E) are used to articulate the distal segment 26 with respect to a longitudinal axis of the proximal segment 20. The distal segment 26 includes electrodes 60 and guard piece 62. The guard piece 62 is connected to a central cable 64 which passes through a longitudinal through-bore of the living hinge 24. Pulling central cable 64 towards a proximal end of device 10 (e.g., by pulling trigger 58 of FIG. 1A) may effectively retract guard piece 62, thereby exposing electrodes 60 for insertion into target tissue. The living hinge 24 may include a sealing plug 25 at its proximal end. At least two electrically conductive wires 61a, 61b (one positive and one negative) are used to deliver the therapeutic energy to the electrodes 60. In addition, a printed circuit board 66 may be positioned perpendicularly to central cable 64 and electrodes 62. In addition, the central cable 64 may include a flexible portion (not shown) that is flexible which allows the central cable 64 to bend when the device is articulated.

Figure 2B:
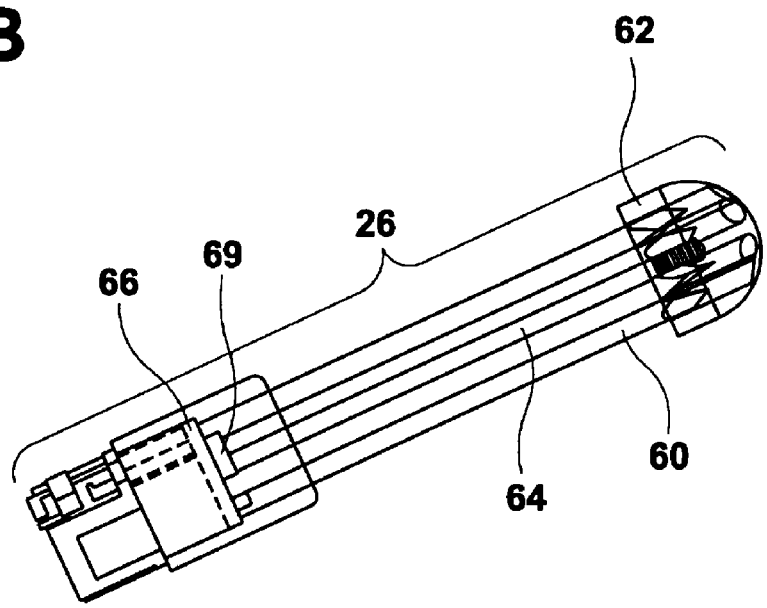
FIG. 2B is a plan view of an additional embodiment of the distal end of the therapeutic energy delivery device of the present invention.

FIG. 2B illustrates an additional embodiment of the distal segment 26 of FIG. 1A. As discussed in greater detail below, the distal segment 26 may include one or more light emitting elements 69 for use as a visual indicator to indicate that the electrodes 60 are delivering the therapeutic energy to the tissue. The distal segment 26 may also include a driver circuit on a printed circuit board 66 having an input coupled to the articulating cables 22a, 22b (see FIGS. 2C-2E) and an output coupled to the light emitting elements 69. The light-emitting members 69 may emit light in a noncontinuous fashion (e.g., flashing with a regular interval) when TED device is in stand-by mode, so as to be differentiated from the continuous light emission during TED mode.

Figure 2C:
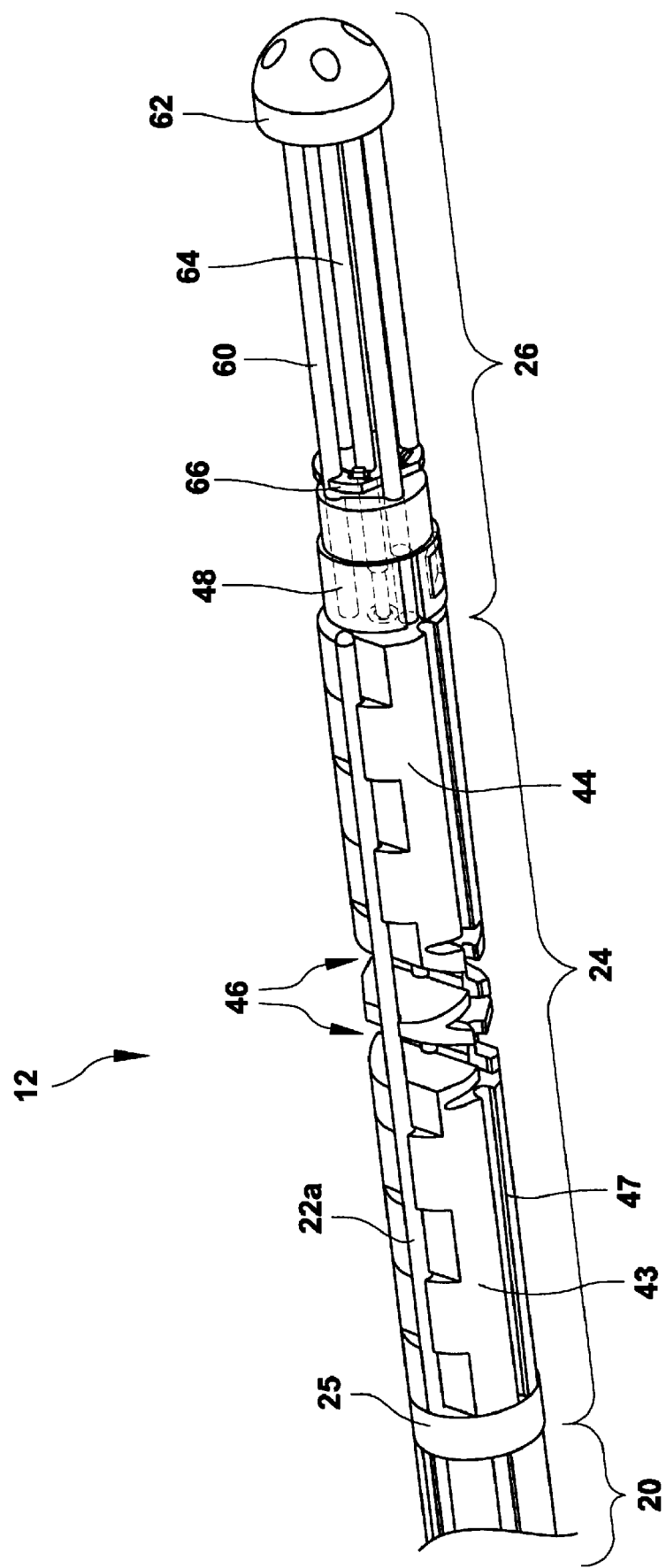
FIG. 2C is a plan view of an additional embodiment of the distal end of the therapeutic energy delivery device of the present invention.

FIG. 2C illustrates an additional embodiment of the treatment member 12 of FIG. 1A. At least two articulating cables 22a, 22b may run along the living hinge 24 to articulate the distal segment 26. In one embodiment, the articulating cables may run along longitudinal side channels of the articulating segment 24. Pulling one or the other articulating cables 22a, 22b proximally in parallel to the longitudinal axis of proximal segment 20 may effectively articulate the distal portion 44 of the living hinge 24, thereby articulating the distal segment 26, from one side to the other. A first articulating cable 22a articulates the distal segment 26 in a first direction; a second articulating cable 22b articulates the distal segment 26 in a second direction. The first articulating cable 22a and second articulating cable 22b are positioned on opposite sides of each other relative to the longitudinal axis of the living hinge 24. It should be noted that the living hinge may include any number of articulating cables, including one, two, three, four or more, wherein the number of articulating cables corresponds generally to the number of articulating directions that are possible. Side channels 47 may be used for housing additional cables if necessary.

In one embodiment, the distal ends of articulating cables 22a, 22b may be coupled (e.g., welded, crimped, etc.) to the proximal ends of at least two of the electrodes 60, so that the articulating cables 22a, 22b are used both to articulate the distal segment 26 and to deliver the therapeutic energy to the electrodes 60. In this embodiment, the articulating cables 22a, 22b consist of an electrically conductive material. For example, a first electrically conductive articulating cable 22a may run along the articulating segment 24, wherein the first articulating cable 22a is used both to articulate the distal segment 26 in a first direction and to deliver the therapeutic energy to at least one positive electrode; a second electrically conductive articulating cable 22b may run along the articulating segment 24, and spaced from the first articulating cable 22a, wherein the second articulating cable 22b is used both to articulate the distal segment 26 in a second direction and to deliver the therapeutic energy to at least one negative electrode. By using the articulating cables to both articulate the distal segment 26 and to deliver the therapeutic energy to the electrodes 60, the number of parts is reduced, thereby reducing the cost of manufacturing the device. In the embodiment shown, electrically conductive wires called "Percon 24" from Fisk Alloy Conductor, Inc. of Hawthorne, N.J., are used.

FIG. 2D illustrates an additional embodiment of the articulating segment 24 of FIG. 1A. Near the middle section of the living hinge 24, there are four longitudinally spaced recessed portions 46 that define where the articulation occurs. As the number of articulating locations is increased, the amount of bending that is required in each respective articulating location is reduced, thereby reducing the localized stresses encountered at the recessed portions 46 with each bend, thereby prolonging the useful life of the device. In this embodiment, a pair of ribs 49 are longitudinally disposed within the living hinge 24, wherein the ribs 49 prevent the distal segment 26 from articulating in a predetermined direction. Further, if the distal portion 44 of the living hinge 24 is somehow articulated in the unintended predetermined direction, the ribs 49 would withstand the stresses and protect the recessed portions 46 of the living hinge 24 against mechanical failure. For example, cross-section wise, if the articulating wires 22a, 22b are placed at zero degree and 180 degrees, respectively, then the two ribs 49 would be placed at 90 degrees and 270 degrees with the planar sides of each rib facing zero degree and 180 degrees.

In the illustrated embodiment, the articulating cables 22a, 22b are not used to deliver the therapeutic energy to the electrodes 60. There are two electrically conductive wires 61a, 61b for delivering the therapeutic energy to the electrodes 60.

FIG. 2E illustrates the articulating segment of FIG. 2D being shown in an articulated position. Here, the second articulating cable 22b has been pulled such that the distal portion 44 of the living hinge 24 is articulated in a second direction.

Figure 3:
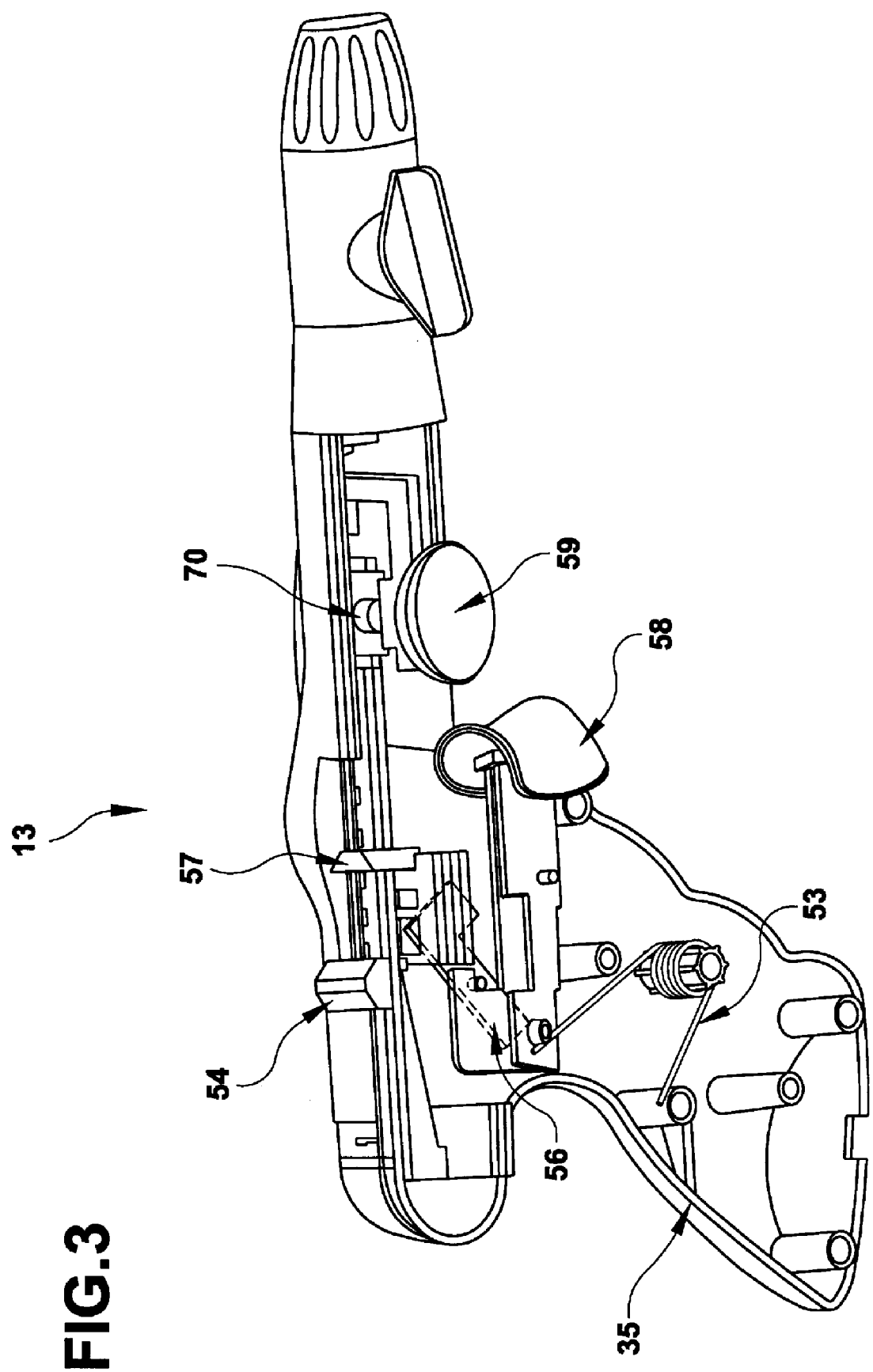
FIG. 3 is a partial cutout perspective view of a base of the therapeutic energy delivery device of the present invention.

FIG. 3 shows certain components housed partially or fully in base 13 of FIG. 1A. Handle 35 may be composed of separately molded pistol-shaped left and right pieces that are coupled together by adhesives or screws. Trigger 58 may be movably coupled with a trigger mechanism 56, which in turn may be movably coupled to trigger slide 57. In combination with central cable 64 (FIGS. 2A-2C), these features allow an operator to retract guard piece 62 and expose pointed electrodes 60 for insertion into target tissue for treatment. The extent of the retraction may be modulated through retraction lock 54, which can slide to allow various partial retraction lengths of guard piece 62, thereby adjusting the length of exposed electrodes 60 for treating target tissues of various sizes. Upon release of the trigger 58, a torsion spring 53 pushes the trigger 58 back to its default position. Because the central cable 64 is attached in-between the slide 57 and the guard piece 62, the guard piece 62 is also returned to its default position upon release of the trigger 58. Switch 70 may be placed adjacent switch actuator 59 such that the operator can depress either side of actuator 59 to turn on or off power supply to the device and the electrodes 60 therein.

Figure 4:
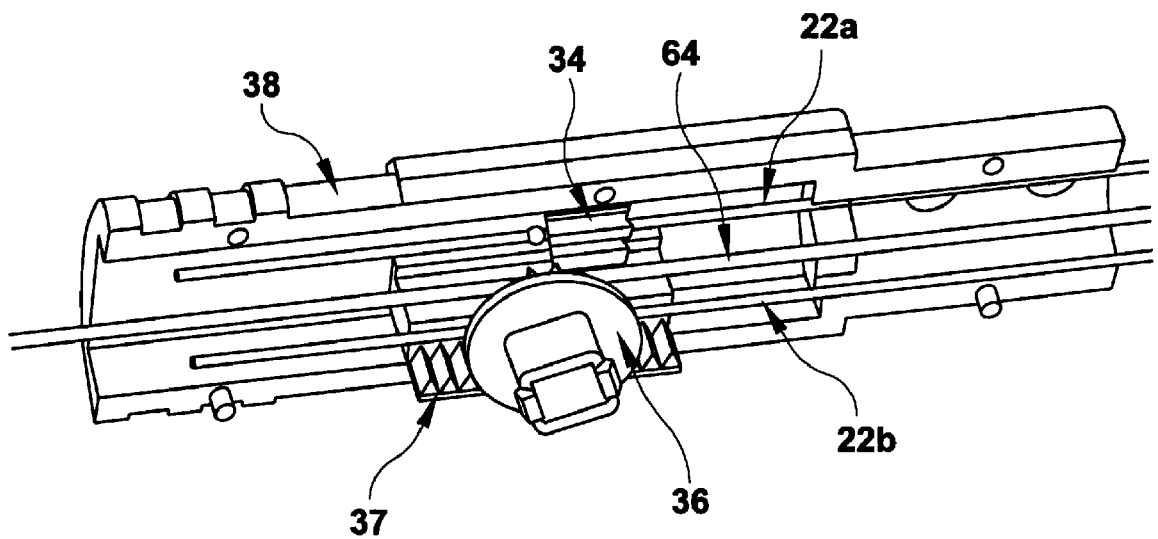
FIG. 4 is a partial cutout perspective view of a rack-and-pinion mechanism of the therapeutic energy delivery device of the present invention.

FIG. 4 illustrates a rack-and-pinion mechanism of the therapeutic energy delivery device of the present invention. The rack-and-pinion mechanism is connected to the proximal ends of the articulating cables 22a, 22b. The rack-and-pinion mechanism is adapted to pull the articulating cables 22a, 22b to articulate the distal segment 26 (FIG. 1A). Turning knob 33 (FIG. 1A) may be detachably coupled to an adapted side of pinion 36, which in turn is adapted (e.g., through complementary teeth) on an opposite side to a pair of racks 37 arranged in parallel to face each other. Racks 37 may be positioned within a generally tubular housing 38, such that racks 37 move in parallel but opposite directions along the housing 38 when pinion 36 is rotated by turning knob 33. This motion may be utilized to pull one of the articulating cables 22a, 22b to articulate the distal segment 26 (FIG. 1A) with respect to the proximal segment 20 (FIG. 1A), as described herein. Cable truck 34 may work in conjunction with bulges along articulating cables 22a, 22b to tighten and secure articulation cables 22a, 22b in the racks 37. The rack-and-pinion mechanism is capable of reticulating the distal segment 26 (FIG. 1A) about the longitudinal axis of the proximal segment 20 over a radial angle of at least 90 degrees, such as 120 degrees or greater, or 150 degrees or greater, or 180 degrees or greater.

The combination of the reticulating motion and the articulating motion allows the distal segment 26 to cover not only a two-dimensional circular sector, but rather a three-dimensional spheroidal sector, such as substantially an entire hemisphere. Such wide range of motions maximizes the degree of freedom an operator enjoys when positioning the device into hard-to-reach target tissues. This minimizes the need for repeated treatment.

Figure 5:
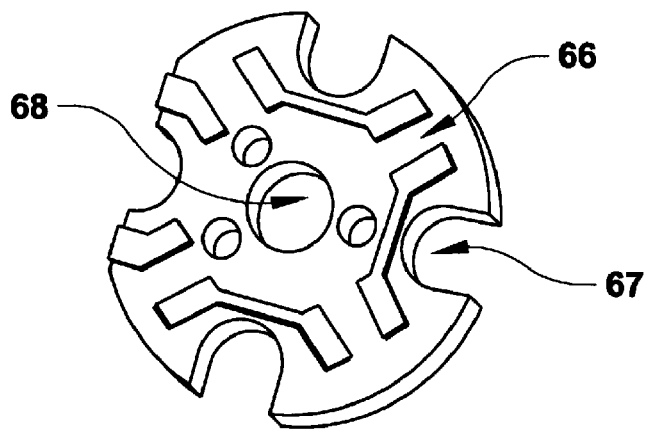
FIG. 5 is a schematic view of a printed circuit board (PCB) of the therapeutic energy delivery device of the present invention.
Figure 6A:
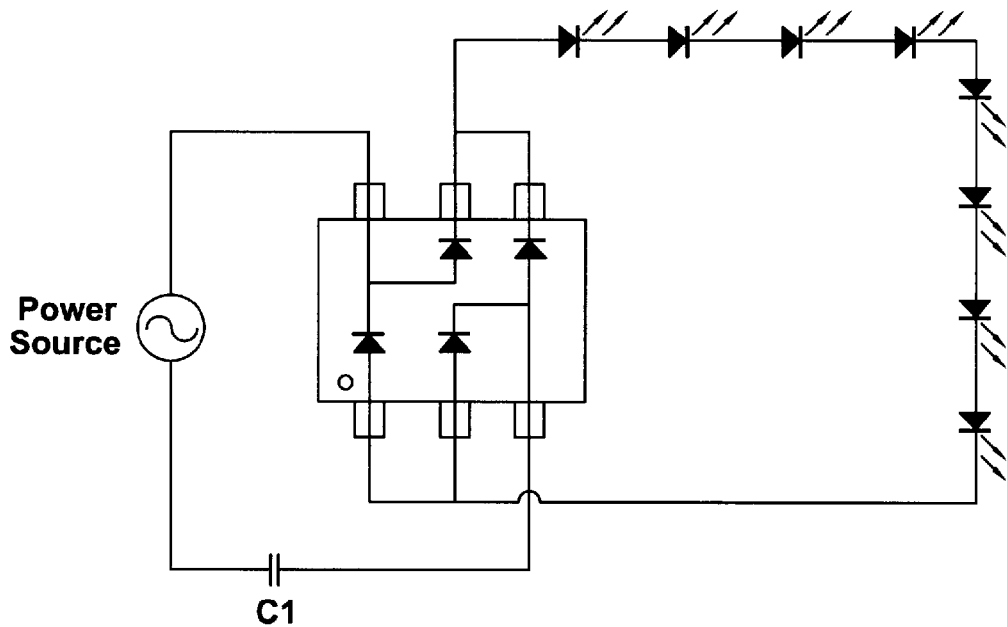
FIG. 6A is a circuit diagram of a lighting device for a medical probe according to one embodiment of the present invention.
Figure 6B:
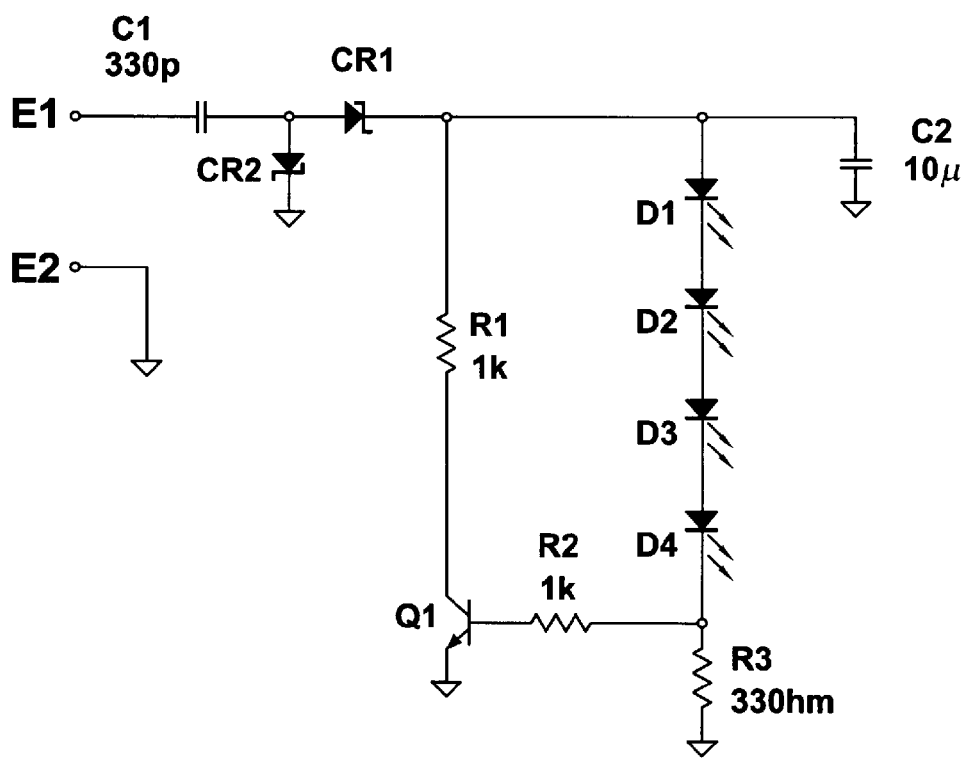
FIG. 6B is a circuit diagram of a lighting device for a medical probe according to another embodiment of the present invention.
Figure 6C:
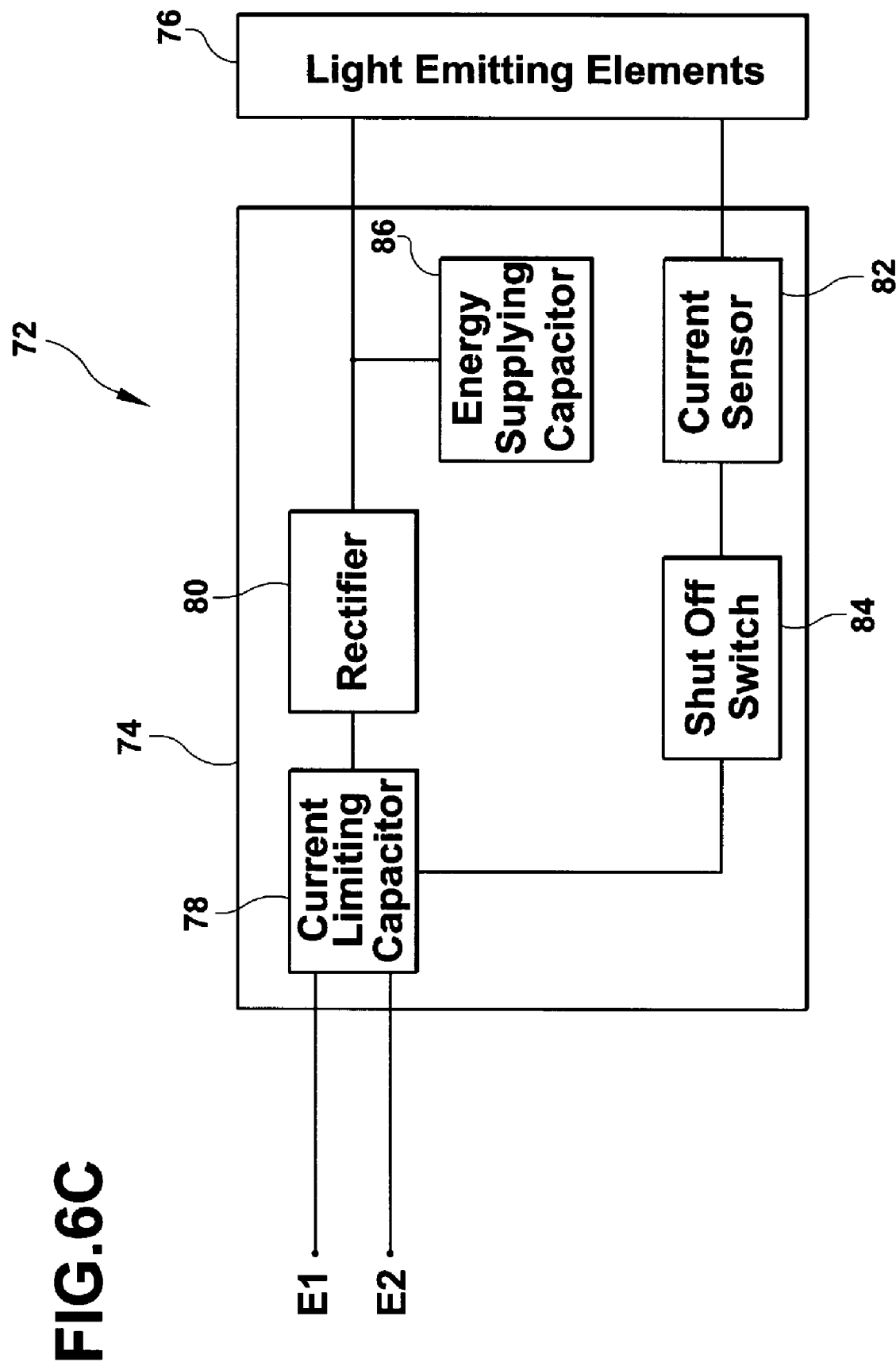
FIG. 6C is a functional block diagram of a lighting device for a medical probe according to another embodiment of the present invention.

FIG. 5 illustrates a printed circuit board 66 of the present invention which contains a driver circuit 74 (see FIG. 6C). Its purpose is described in greater detail below. The lines illustrate the printed circuitry. Central through-bore 68 may allow rod 64 (FIG. 2A-2C) to pass through. Peripheral slots 67 may allow electrodes 60 (FIG. 2A-2C) to pass through. A portion of the printed circuitry may be in direct contact with at least one of the electrodes 60 that passes through the printed circuit board 66.

As shown in FIG. 6, the input terminals E1 and E2 are adapted to receive RF energy from a power source (not shown). The RF energy is either a test energy or therapeutic energy. In one embodiment, the therapeutic energy is a 460 kHz RF signal provided to the electrodes. The voltage can vary from 15 volts to 135 volts rms (+200 volt to −200 volt peak-to-peak) depending on the treatment level of a particular patient. The test energy is a 100 milisecond long, 460 kHz, 32 volts rms RF signal sent once a second to the electrodes. Both test and therapeutic energy signals are sinusoidal signals in the embodiment shown. While the medical probe is in a ready mode and not in an operating mode, the test energy signal is used to determine whether the medical probe is inserted into the tissue or not by monitoring the impedance across the electrodes. If the operator activates the medical probe 10 while it is outside of the tissue, the energy source is prevented from supplying the therapeutic energy to the electrodes.

According to one embodiment of the present invention, the RF energy provided to the electrodes for treating a patient is also used to power one or more light emitting elements that are preferably positioned near the distal end of the medical probe 10. The lighting elements are used by the physician as a visual indicator. If the lighting elements are lit continuously, that means the medical probe is in an operating mode in which the therapeutic energy is being applied to the target tissue. If the lighting elements are blinking, e.g., lit for a very short time (e.g., one tenth of a second) every second, that means the medical probe is in a standby in which the therapeutic energy is not being applied to the target tissue.

FIG. 6A illustrates one lighting device for the medical probe 10 that runs on DC and is adapted to be positioned within the treatment member 12 (FIG. 1A). The therapeutic energy from the power source is fed to a full-wave rectifier (shown inside a chip) to produce DC. The DC current drives a series of light emitting diodes (eight as shown). Each diode as shown needs about 3 volts to turn on. The capacitor C1 acts as a current limiting capacitor to limit the current and power dissipation of the light emitting diodes.

One disadvantage of this design is that at a relatively low treatment level (lower therapeutic energy level) or on standby, the light emitting diodes are dim making it difficult for the physician to see while at a high treatment level, the diodes may be very bright.

FIG. 6B shows another lighting device for the medical probe 10. The RF energy from a power source is provided at input terminals E1 and E2. A capacitor C1 is a current limiting capacitor that limits the current being provided to light emitting elements D1-D4. Each of the light emitting elements D1-D4 is a light emitting diode with a driving voltage of about 3 volts. The two diodes CR1, CR2 connected to the current limiting capacitor C1 are a half-wave rectifier that converts the RF therapeutic energy at terminals E1, E2 into DC. A resistor R3 connected between the diode D4 and ground is a current sensing resistor that senses the current flowing through the diodes D1-D4. Resistors R1 ,R2 and transistor Q1 act as a shunt circuit to dump excess current when the current through the resistor R3 reaches a predetermined threshold level.

For example, when the current reaches about 20 mili-amps, the transistor Q1 begins to turn on and any current in excess of 20 mili-amps is dumped to ground through the resistor R1 and transistor Q1. When the transistor Q1 is on, the RF therapeutic energy is providing DC current to both the resistor R1 and diodes D1-D4. One disadvantage for this circuit is that the resistor R1 becomes very hot. This makes it unsuitable to house the circuit in a very small area within the treatment member 12 of the medical probe 10.

Figure 6D:
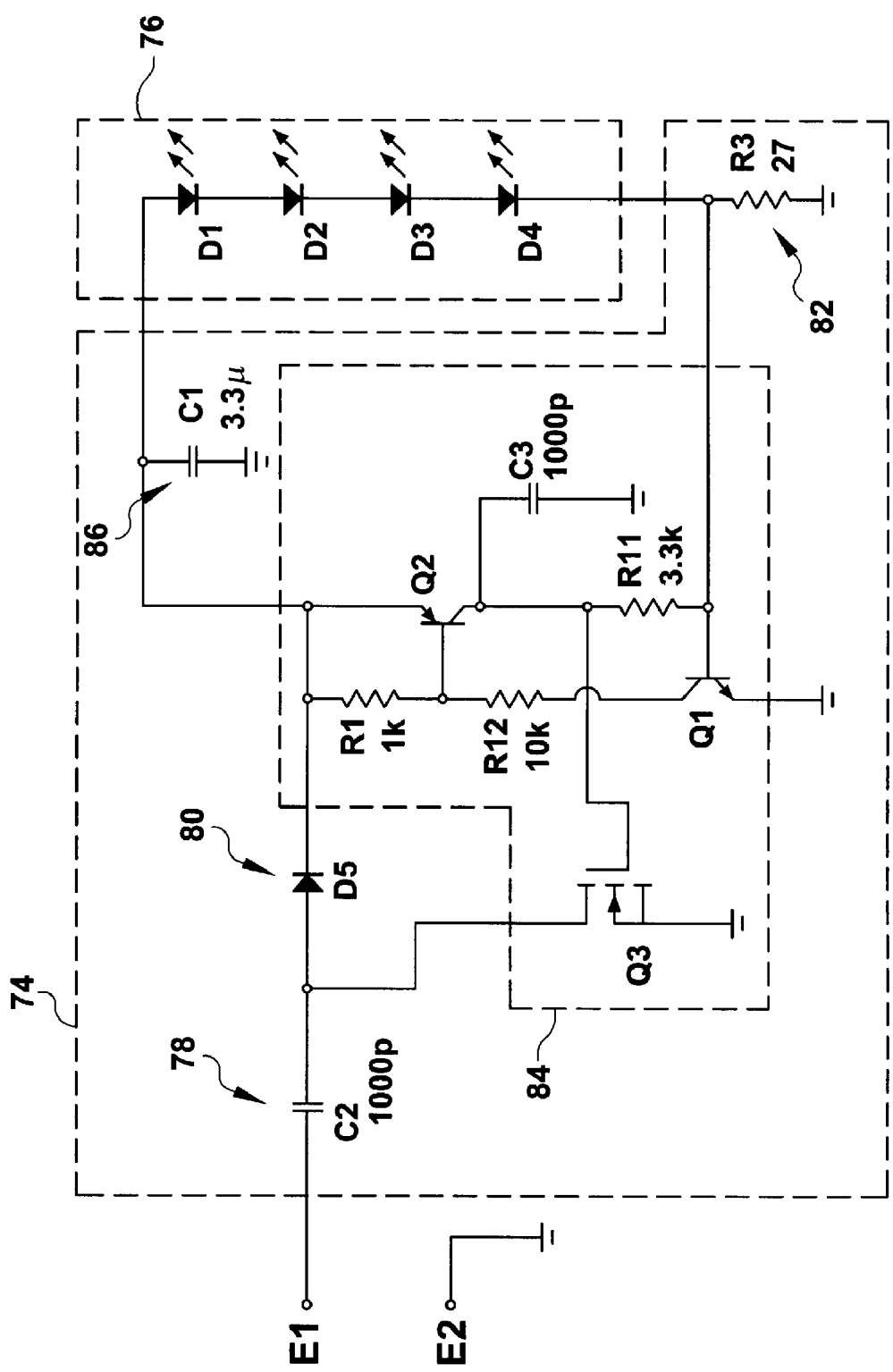
FIG. 6D is a circuit diagram for the lighting device of FIG. 6C.

FIG. 6C illustrates a functional block diagram of another lighting device 72 design and FIG. 6D illustrates a detailed circuit design of the lighting device of FIG. 6C. The lighting device 72 includes a set of light emitting elements 76 that are driven by a driver circuit 74. The driver circuit 74 is powered by RF energy from a power source which is provided at input terminals E1 and E2. As discussed above, the power source outputs either the test energy or therapeutic energy both being a 460 kHz RF signal. A current limiting capacitor 78, which acts as an impedance to the AC signal being provided from the input terminals E1, E2, limits the current provided to light emitting elements 76 which are connected in series with each other. Each of the light emitting elements D1-D4 is a light emitting diode with a driving voltage of about 3 volts. A rectifier 80 connected to the current limiting capacitor 78 is a half-wave rectifier that converts the RF therapeutic energy or test energy at terminals E1, E2 into DC. The rectifier 80 includes diode D5 and a hidden diode within a transistor Q3. A current sensor 82 which includes a resistor R3 is connected between the light emitting elements 76 and ground. A shut off switch 84 comprises a field effect transistor (FET) Q3, transistors Q1, Q2, resistors R1, R12 and R11, and capacitor C3. An energy supplying capacitor 86 is connected between the input of the light emitting elements 76 and ground.

In operation, the RF signal at the input terminals E1, E2 is converted to a DC signal by the rectifier 80. The DC signal charges the energy supplying capacitor 86. When the capacitor 86 is charged to about 12 to 13 volts, the light emitting elements 76 turn on. The light emitting elements 76 are used as a visual indicator to a physician that the medical probe 10 is either in the active mode in which case the lights are lit continuously or in the standby mode in which case the light emitting elements would flash every second.

The current sensor 82 senses the current flowing through the diodes D1-D4. When the current reaches a predetermined threshold level, e.g., about 22 milli-amps (about a 0.6 volt drop across the 27 Ohm sensing resistor R3), the shut off switch 84 shuts off the power source current from the diodes D1-D4. Specifically, the current sensor 82 turns on the transistor Q1, which turns on the transistor Q2 which turns on the transistor Q1 very hard, essentially locking each other transistor on. In the process, it turns on the FET transistor Q3. This connects the current limiting capacitor 78 to ground so that the power source connected to the input terminals is no longer supplying any current to the rectifier 80 and the diodes D1-D4.

During that time, the energy supplying capacitor 86 supplies current to the diodes D1-D4. As the capacitor 86 discharges, the current through the diodes D1-D4 falls below the predetermined threshold level. This turns off the transistors Q1, Q2 and Q3 in that sequence. Then, the cycle repeats. Thus, the driver circuit 74 acts as a current regulator to provide a relatively constant current e.g., between about 21-22 milli-amps, to the diodes D1-D4 without wasting any power and therefore without any build up of heat.

As can be appreciated, the lighting device of FIG. 6C provides many benefits. First, there is no power dissipation from the power source while the shut off switch 84 is shutting off the power source current from the diodes D1-D4. This means there is no heat build up in the circuits. Consequently, such an efficient design allows the lighting device to be housed inside a confined space of a medical probe. Second, the driver circuit 74 accommodates a wide range of voltage levels of therapeutic energy. So long as the energy level exceeds the total voltage drops of the diodes D1-D4, which is about 12 volts, the lighting device 72 provides a constant brightness regardless of the treatment energy level. Third, because the driver circuit 74 uses the same power source as that used for treating the patient, there is no need to run separate electrical wires from the RF energy source to the probe, simplifying the design of the probe.

TED devices may be provided in kits that include the device, one or more sets of cables and/or tubing attached or adaptable to the device, and an instruction for use (IFU). IFU may be in accordance with distributor and/or regulatory requirements. IFU may state intended use of the device and associated components, contraindication, warnings, cautions, precautions, and/or restrictions on combinations. For example, a kit may contain a TED 10 device, a set of cables and/or tubing coupled to or is adapted to be coupled to the device, and an instruction for use of the device. The device may contain a treatment member 12 for delivering a therapeutic energy to a target tissue, and at least one of the following: a distal segment 26 of treatment member 12 is articulatable with respect to the remainder of treatment member 12; a rotatable collar 30 coupled to a proximal portion of treatment member 12 for reticulating treatment member 12; and/or a circuitry positioned along a distal segment 26 of treatment member 12 for converting a portion of the delivered therapeutic energy to electric current (e.g., direct current).

Software on a computer-readable medium may be used to control certain aspects of using the devices, such as controlling power (e.g., amplitude, pulse frequency) to the device, analyzing feedback signals from TED segment (e.g., thermal readings, impedance, visual signals), and providing signals for actions (e.g., readiness, stand-by, power-on, power-off, warnings, failure signals). For example, a software package stored or installed on a computer-readable medium may be used for facilitating and/or enabling the methods and/or processes of using the TED devices.

Methods and processes of using the devices disclosed herein may involve one, two, or more of the following actions, in serial and/or in parallel with each other. Specifically, the treatment member 12 of the devices may be introduced into a patient. The device may contain a collar 30 proximal to treatment member 12 and be coupled thereto in a fashion such that reticulation of collar 30 causes simultaneous reticulation of treatment member 12 about its longitudinal axis. Treatment member 12 may further contain an articulatable segment 26. Articulatable segment 26 may further contain a plurality of electrodes 60 with their pointed tips embedded in a guard piece 62. Articulatable segment 26 may be aligned to a target tissue such that a distance between the target tissue and articulatable segment 26 is shorter than the longitudinal length of the articulatable segment 26. Collar 30 may be reticulated by an operator to reticulate treatment member 12 such that at least one plane of articulation of articulatable segment 26 passes through the target tissue. Articulatable segment 26 may then be articulated such that guard piece 62 is positioned adjacent to the target tissue. Guard piece 62 may be retracted in a proximal direction to expose at least a portion of electrodes 60. Electrodes 60 are then inserted into the target tissue. A therapeutic energy may be delivered from electrodes 60 to the target tissue. A portion of the delivered therapeutic energy may be converted to electric current (e.g., direct current) through a circuitry positioned along electrodes 60. The electric current continuously powers one or more light-emitting members 69 positioned along articulatable segment 26 to emit visible light for as long as the therapeutic energy is delivered from electrodes 60. The method results in at least one resection, excision, coagulation, disruption, denaturation, or ablation of the target tissue. Following the treatment, guard piece 62 may be allowed to return to the position effective in shielding the pointed tips of electrodes 60. Articulatable segment 26 may be articulated to be in straight line with respect to the remainder of treatment member 12. Treatment member 12 may then be safely removed from the patient without causing unintended effects.

TED devices disclosed herein are designed for tissue destruction in general, such as resection, excision, coagulation, disruption, denaturation, and ablation, and are applicable in a variety of surgical procedures, including but not limited to open surgeries, minimally invasive surgeries (e.g., laparoscopic surgeries, endoscopic surgeries, surgeries through normal body orifices), thermal ablation surgeries, non-thermal surgeries, as well as other procedures known to one of ordinary skill in the art. The devices may be designed as disposables or for repeated uses. The devices enable the operator to reach lines of resection that are inaccessible with non-articulated devices, and/or inform the operator instantaneously that TE is actually delivered to the target tissue.

TEC to DC onboard the TED device as described herein may be used to power a variety of signaling, diagnostic, and/or therapeutic electronic components, without requiring dedicated power wires to pass through the longitude of treatment member 12 (including the articulation segment 24) and additional pressure seal, thus allowing the implementation of various functionalities into the device to enhance the value of the device without significantly increasing its construction complexity (e.g., extra cables, and the likes thereof). Non-limiting examples of such electronic components include indicator lights, lights for visualization, diagnostic lights or electricity, and micro-electro-mechanical systems (MEMS, including sensor and emitters such as LEDs). In one example, the electronic component may be a miniaturized computer with a MEMS sensor, which may be placed near or on a tissue of interest to obtain various measurements (e.g., temperature, impedance, oxygen level). Such an electronic component may be powered by TE or electricity converted from TE, and may be able to send signals back (e.g., along TE wires or other wires) to the control system (as a feedback mechanism). In addition, such functionalities (e.g., electronic components) may be modularized and therefore scalable, so that the operator or hospital can reduce cost of ownership by using the same core devices and purchasing optional modules as the need arises. In one example, a DC-powered electronic component may be incorporated into the TED device for imaging light reflection in tissues for analyses of such non-limiting parameters as oxygen levels and tissue health. When light-emitting members 69 are used as primary light sources within the vicinity of distal segment 26, they may be positioned such that light is emitted in distal and/or radial directions as illustrated herein. When other functionalities, such as imaging (e.g., through the use of a camera), is also implemented along distal segment 26, light-emitting members 69 may be arranged to emit light in proximal (e.g., facing the camera) and/or radial directions.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed is:

1. A device for delivering therapeutic energy to tissue, comprising:
   a proximal segment;
   a distal segment having a longitudinal axis and one or more electrodes for delivering the therapeutic energy to the tissue, wherein a plurality of electrodes extends distally from the distal segment along a plurality of axes, and wherein at least one of the axes is parallel to the longitudinal axis of the distal segment, wherein at least one of the plurality of electrodes is capable of piercing the tissue; and
   a living hinge connecting the proximal segment and the distal segment such that the distal segment is articulatable with respect to a longitudinal axis of the proximal segment.

2. The device of claim 1, wherein the living hinge includes at least one recessed portion that defines where the articulation occurs.

3. The device of claim 1, wherein the living hinge includes two longitudinally spaced recessed portions that define where the articulation occurs.

4. The device of claim 1, wherein the living hinge includes four longitudinally spaced recessed portions that define where the articulation occurs.

5. The device of claim 1, further comprising:
   a base attached to the proximal end of the proximal segment; and
   a collar rotatably coupled to the base, wherein rotation of the collar rotates the proximal segment about the longitudinal axis.

6. The device of claim 1, further comprising: at least one articulating cable running along the living hinge to articulate the distal segment.

7. The device of claim 1, further comprising:
   a first articulating cable running along the living hinge to articulate the distal segment in a first direction: and
   a second articulating cable running along the loving hinge, spaced from the first articulating cable, to articulate the distal segment in a second direction.

8. The device of claim 7, wherein the first and second articulating cables are positioned on opposite sides of each other relative to the longitudinal axis.

9. The device of claim 6, further comprising: a rack-and-pinion mechanism connected to a proximal end of the at least one articulating cable and adapted to pull the at least one articulating cable to articulate the distal segment.

10. The device of claim 1, further comprising a pair of ribs longitudinally disposed within the living hinge, wherein the ribs prevent the distal segment from articulating in a predetermined direction.

11. A device for delivering therapeutic energy to tissue, comprising:
   a proximal segment;
   a distal segment having a longitudinal axis and one or more electrodes for delivering the therapeutic energy to the tissue, wherein a plurality of electrodes extends distally from the distal segment along a plurality of axes, and wherein at least one of the axes is parallel to the longitudinal axis of the distal segment;
   an articulating segment connecting the proximal segment and the distal segment such that the distal segment is articulatable with respect to a longitudinal axis of the proximal segment; and
   at least one electrically conductive articulating cable running along the articulating segment, wherein the articulating cable is used both to articulate the distal segment and to deliver the therapeutic energy to the one or more electrodes.

12. The device of claim 11, wherein the at least one electrical conductive articulating cable is disposed along the outside of the articulating segment.

13. The device of claim 11, wherein the articulating segment includes a living hinge.

14. The device of claim 11, further comprising:
   a base attached to the proximal end of the proximal segment; and
   a collar rotatably coupled to the base, wherein rotation of the collar rotates the proximal segment about the longitudinal axis.

15. The device of claim 11, further comprising:
   a rack-and-pinion mechanism connected to a proximal end of the at least one electrically conductive articulating cable to pull the articulating cable to articulate the distal segment.

16. The device of claim 11, further comprising a pair of ribs longitudinally disposed within the articulating segment, wherein the ribs prevent the distal segment from articulating in a predetermined direction.

17. A device for delivering therapeutic energy to tissue, comprising:
   a proximal segment;
   a distal segment having at least one positive electrode and at least one negative electrode for delivering the therapeutic energy to the tissue;
   a distal segment having a longitudinal axis and one or more electrodes for delivering the therapeutic energy to the tissue, wherein a plurality of electrodes extends distally from the distal segment along a plurality of axes, and wherein at least one of the axes is parallel to the longitudinal axis of the distal segment;
   an articulating segment connecting the proximal segment and the distal segment such that the distal segment is articulatable with respect to a longitudinal axis of the proximal segment;
   a first electrically conductive articulating cable running along the articulating segment, wherein the first articulating cable is used both to articulate the distal segment in a first direction and to deliver the therapeutic energy to the at least one positive electrode; and
   a second electrically conductive articulating cable running along the articulating segment, and spaced from the first articulating cable, wherein the second articulating cable is used both to articulate the distal segment in a second direction and to deliver the therapeutic energy to the at least one negative electrode.

18. The device of claim 17, wherein the distal segment includes one or more light emitting elements for use as a visual indicator to indicate that the one or more electrodes are delivering the therapeutic energy to the tissue.

19. The device of claim 18, wherein the distal segment includes a driver circuit, having an input coupled to the articulating cable and an output coupled to the light emitting elements.

* * * * *